United States Patent [19]

Wahlstrand et al.

[11] Patent Number: 5,402,794
[45] Date of Patent: Apr. 4, 1995

[54] METHOD AND APPARATUS FOR HEART TRANSPLANT MONITORING AND ANALOG TELEMETRY CALIBRATION

[75] Inventors: John D. Wahlstrand, Shoreview; Peter M. J. Mulier, St. Paul; David L. Thompson, Fridley, all of Minn.;

[73] Assignee: Medtronic, Inc., Minneapolis, Minn.

[21] Appl. No.: 907,259

[22] Filed: Jul. 1, 1992

[51] Int. Cl.⁶ .......................................... A61N 1/372
[52] U.S. Cl. ..................... 128/696; 607/32
[58] Field of Search ......... 128/419 P, 419 PG, 419 T, 128/696, 700, 782, 903; 340/573, 502–505; 371/2.1, 4; 607/19, 32, 60, 145, 27

[56] References Cited

U.S. PATENT DOCUMENTS

| | | |
|---|---|---|
| 4,503,858 | 3/1985 | Markowitz . |
| 4,505,276 | 3/1985 | Markowitz . |
| 4,556,063 | 12/1985 | Thompson et al. ................. 128/419 |
| 4,618,861 | 10/1986 | Gettens et al. ....................... 128/903 |
| 5,052,388 | 10/1991 | Sivula et al. ................. 128/419 PG |
| 5,127,404 | 7/1982 | Wyborny et al. ............... 128/419 P |
| 5,139,028 | 8/1992 | Steinhaus et al. ................... 128/697 |
| 5,157,604 | 10/1992 | Axfovd et al. ................. 364/413.03 |

FOREIGN PATENT DOCUMENTS

| | | |
|---|---|---|
| 0002213 | 11/1978 | European Pat. Off. ........ A61N 1/36 |
| 0159753 | 10/1985 | European Pat. Off. . |
| 0268708 | 6/1988 | European Pat. Off. . |
| 0412427 | 2/1991 | European Pat. Off. ..... H04L 27/06 |
| 0443496 | 8/1991 | European Pat. Off. ..... A61N 1/372 |
| 4029961 | 10/1991 | Germany . |
| 8903234 | 4/1989 | WIPO ............................. A61N 1/36 |

OTHER PUBLICATIONS

Grace et al., "Diagnosis of Early Cardiac Transplant Rejection by Fall in Evoked T Wave Amplitude Measured Using an Externalized QT Driven Rate Responsive Pacemaker", PACE, vol. 14, Jun. 1991 pp. 1024–1031.

Kriett, et al., "The Registry of the International Society for Heart and Lung Transplantation: Eighth Official Report-1991", The Journal Of Heart And Lung Transplantation, Jul./Aug. 1991, pp. 491–498.

Rosenbloom et al., "Noninvasive Detection of Cardiac Allograft Rejection by Analysis of the Unipolar Peak-to-Peak Amplitude of Intramyocardial Electrograms", Ann. Thorac. Surg., 1989;47:407–411.

Warnecke, et al., "Noninvasive monitoring of cardiac allograft rejection by intramyocardial electrogram recordings", Circulation 74, (supp III), III-72–III-76, 1986.

Primary Examiner—William E. Kamm
Assistant Examiner—Marianne Parker
Attorney, Agent, or Firm—Harold R. Patton

[57] ABSTRACT

A cardiac pacemaker with an analog telemetry system. A calibration circuit within the pacemaker is adapted to provide a reference signal of known character to the pacemaker's telemetry system. The reference signal is transmitted across the telemetry link as if it were an actual cardiac signal, and received by an external programmer. Since the reference signal has known, predetermined qualities, the programmer can automatically calibrate and scale the telemetry signal from the pacemaker, thereby increasing the accuracy of the telemetry channel. The increased accuracy is particular useful in assessing rejection of a transplanted heart, which is known to be associated with a 15% decline in the peak R-wave amplitude of the cardiac signal.

9 Claims, 8 Drawing Sheets

METHOD AND APPARATUS FOR HEART TRANSPLANT MONITORING AND ANALOG TELEMETRY CALIBRATION

FIELD OF THE INVENTION

This invention relates to the field of cardiac pacemakers, and more particularly to a pacemaker having an automatic calibration signal for an analog telemetry channel.

BACKGROUND OF THE INVENTION

As of Jan. 1, 1991, over 16,000 heart transplants have taken place worldwide, more than 87% of these since 1984 (according to Kreitt et al., "The Registry of the International Society for Heart and Lung Transplantation: Eight Annual Report", *The Journal of Heart and Lung Transplantation*, Number 4, Jul.-Aug. 1991, pp. 491-498). Rejection of the transplanted heart within two years is the cause of death in 40% or more of all cases. Currently, the preferred method for monitoring rejection is by serial transvenous endomyocardial biopsy. Such a procedure is invasive and relatively traumatic, and must usually be performed at specialized facilities. Typically, two such tests are performed during the first six post-implant months; thereafter, the tests are given less frequently, but throughout the patient's lifetime. Up to a day may be required to obtain results from such a test. One known shortcoming of the serial transvenous endomyocardial biopsy in evaluating heart rejection is that existing scar tissue in the heart, which can occur for various reasons other than heart rejection, can be erroneously interpreted as indicating rejection.

It has also been found, however, that certain features of the electrical cardiac signal in transplant patients may also be utilized as an indicator of heart rejection. See, e.g., Warnecke et al., "Noninvasive Monitoring of Cardiac Allograft Rejection by Intramyocardial Electrogram Recordings", *Circulation* 74 (*suppl. III*), III-72-III-76, 1986. In particular, it has been found that the onset of heart rejection is accompanied by a reduction of up to 15% in the magnitude of intracardiac R-wave and T-wave peaks. See, e.g., Rosenbloom et al., "Noninvasive Detection of Cardiac Allograft Rejection by Analysis of the Unipolar Peak-to-Peak Amplitude of Intramyocardial Electrograms", *Ann. Thorac. Surg.*, 1989; 47:407-411; see also, e.g., Grace et al., "Diagnosis of Early Cardiac Transplant Rejection by Fall in Evoked T Wave Amplitude Measured Using an Externalized QT Driven Rate Responsive Pacemaker", *PACE*, vol. 14, Jun. 1991. The ability to monitor and detect this phenomenon would therefore facilitate the early detection and treatment of rejection. To this end, an implantable pacemaker with an accurate analog telemetry channel for transmitting intracardiac signals would greatly enhance the ability of a monitoring physician to assess the cardiac condition.

Intracardiac electrogram signals have been used to evaluate heart rejection. Typically, however, several or perhaps up to five or more epicardial leads may be used for this purpose, since it is believed that the manifestations of heart rejection are initially localized and can begin at various sites in the heart muscle.

The intracardiac leads associated with an implanted pacemaker might also be used in the evaluation of cardiac signals. Unfortunately, even today's state-of-the-art pacemakers have rather inaccurate telemetry channels, varying greatly in their response from one device to another and susceptible to problems with drift, change with temperature, and battery condition. The inaccuracies in the peripheral (programmer) can compound the pacemaker and telemetry channel errors. In some cases, the accuracy of a telemetered intracardiac EGM signal from an implanted pacemaker may be only ±35%.

SUMMARY OF THE INVENTION

It is believed by the inventors, therefore, that it would be desirable to provide a more accurate analog telemetry channel for an implantable cardiac pacemaker, so that an accurate and reliable assessment of cardiac activity can be made. In accordance with the present invention, a signal is provided to automatically calibrate a pacemaker's analog telemetry channel. The increased accuracy of the telemetered EGM signal would allow it to be used not only in transplant rejection monitoring, but also for measuring amplitude and slew rate in cardiac signals, evaluation of lead maturation effects, general pacemaker system troubleshooting, and congestive heart failure (CHF) monitoring.

In accordance with one embodiment of the present invention, a known and accurate test signal at the lead tip electrode is transmitted through the telemetry channel, allowing the external programmer or other peripheral to automatically calibrate and auto-range the entire telemetry system, which includes the pacemaker filtering circuitry, pacemaker gain control circuitry, a voltage-to-frequency converter or some other type analog-to-digital converter, a data encoder, radio frequency link, a data decoder, and signal reconstruction and display circuitry.

BRIEF DESCRIPTION OF THE DRAWINGS

The foregoing and other aspects of the present invention will be best understood with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
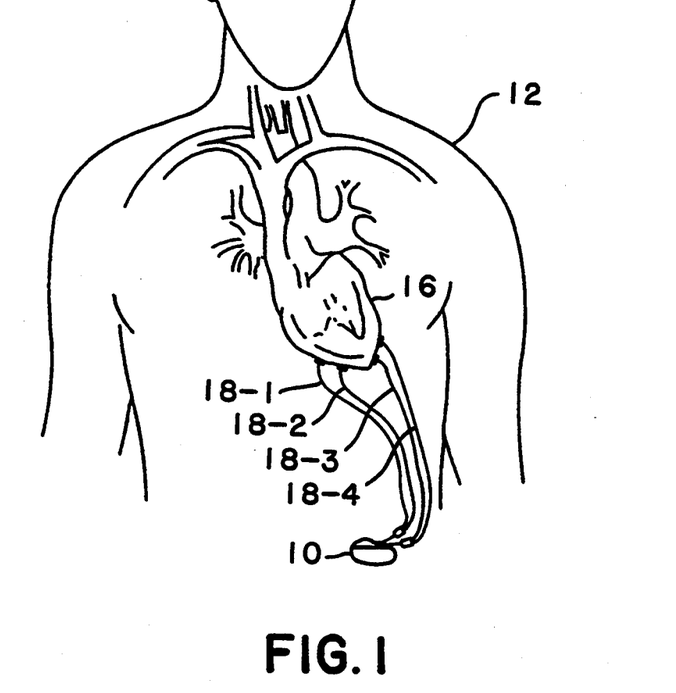
FIG. 1 is an illustration of a pacemaker and pacemaker leads in accordance with one embodiment of the present invention, implanted in a patient.

In FIG. 1, a pacemaker 10 in accordance with one embodiment of the present invention is shown implanted in a patient 12. Pacemaker 10 is electrically coupled to heart 16 of patient 12 by means of four unipolar epicardial leads 18-1, 18-2, 18-3, and 18-4. One pacemaker which may be readily adapted for use in accordance with the presently disclosed embodiment of the invention is disclosed in U.S. Pat. No. 5,052,388 issued to Sivula et al. on Oct. 1, 1991, which patent is hereby incorporated by reference in its entirety. It is believed by the inventors, however, that from the following detailed description of a specific embodiment of the present invention it should be apparent to a person of ordinary skill in the pacemaker art how the present invention may be practiced in conjunction with a variety of known pacemaker designs.

Figure 2:
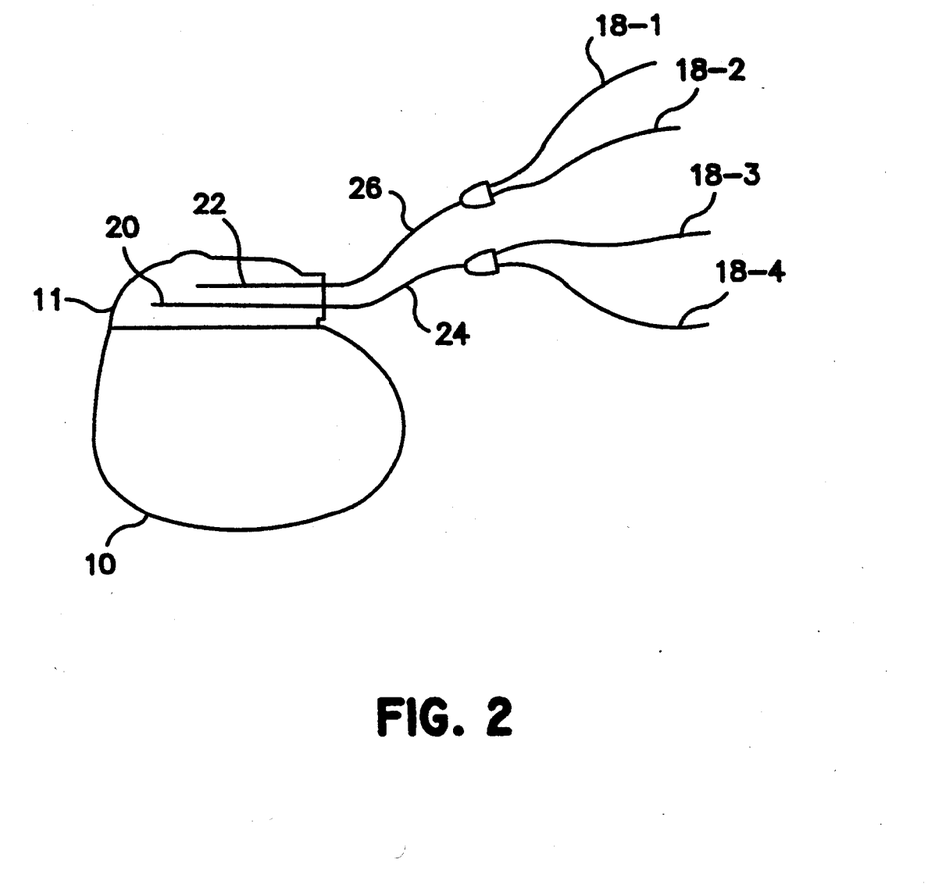
FIG. 2 is an illustration of the pacemaker and leads from FIG. 1.

As shown in FIG. 2, pacemaker 10 is provided with a connector block 11 for receiving connector pins 20 and 22 of two "IS-1 to bifurcated" adapters 24 and 26. Adapters 24 and 26 allow the four unipolar leads 18-1, 18-2, 18-3, and 18-4 to be interfaced with industry standard IS-1 connection points in dual bipolar connector block 11. Leads 18-1, 18-2, 18-3, and 18-4 may be Medtronic Models 5069 or 5071 Unipolar Epicardial leads or the like. Adapters 24 and 26 may be, for example, Model 5866-24M IS-1 to bifurcated adapters manufactured and commercially available from Medtronic, Inc., Minneapolis, Minn. In an alternative embodiment, a connector block 11 capable of receiving all four leads 18-1, 18-2, 18-3, and 18-4 could be provided, thereby eliminating the need for adapters 24 and 26.

Figure 3:
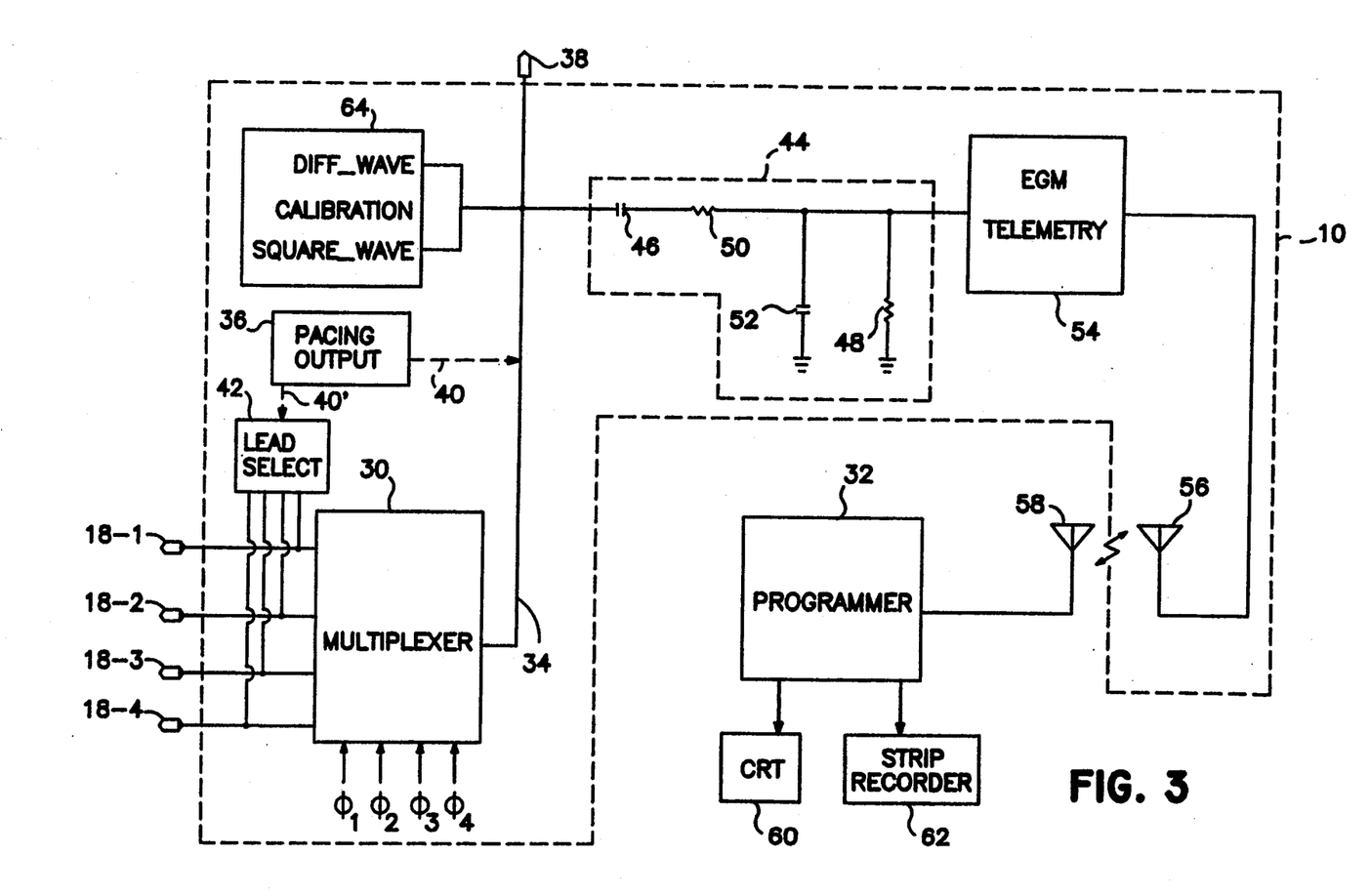
FIG. 3 is a block diagram showing a portion of the circuitry of the pacemaker of FIG. 1 and an external programmer.

Turning now to FIG. 3, a block diagram showing selected relevant portions of internal circuitry of pacemaker 10, as well as an external programmer 32 which communicates with pacemaker 10 via a radio-frequency telemetry link. In FIG. 3, leads 18-1, 18-2, 18-3, and 18-4 are shown being directly connected to a multiplexer 30 in pacemaker 10, it being understood that adapters 24 and 26 may be required to facilitate the connection of four leads to pacemaker 10, as previously described with reference to FIG. 2.

Figure 4:
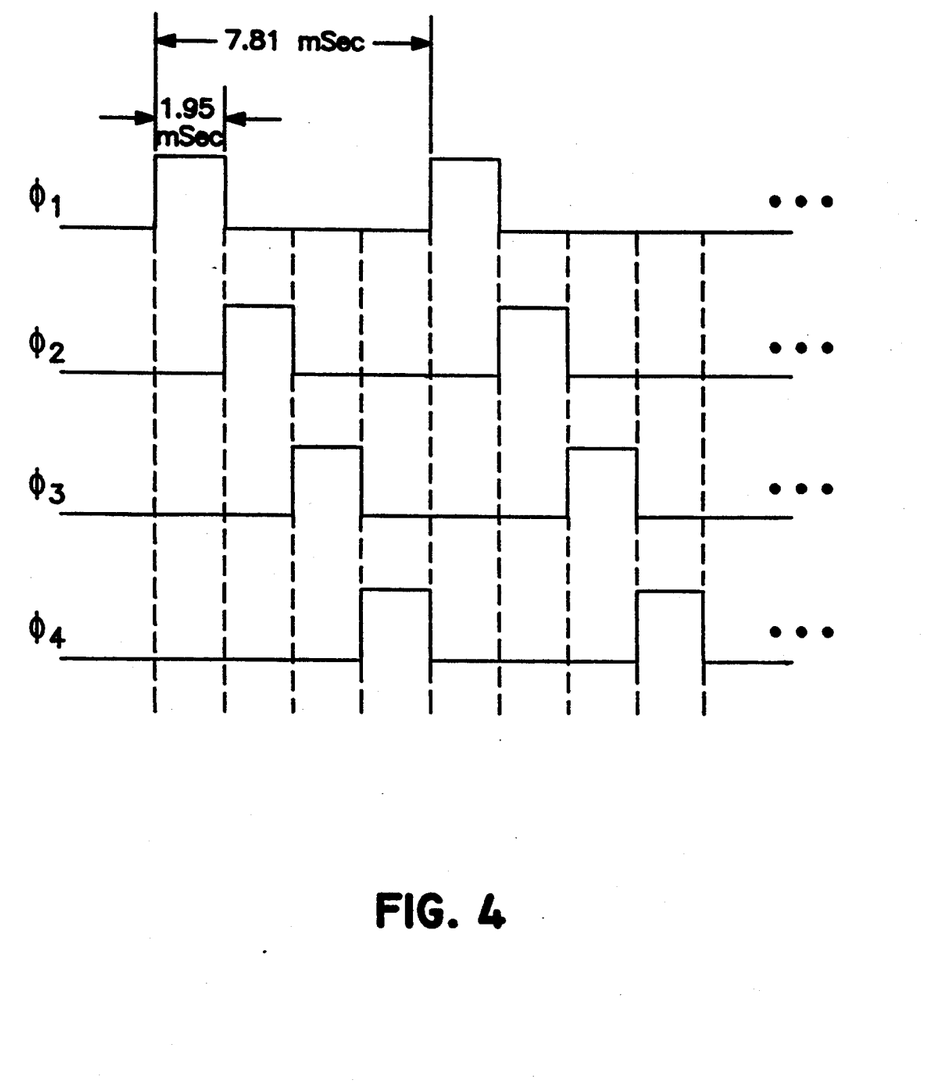
FIG. 4 is a timing diagram illustrating clock signals utilized by the circuitry of FIG. 3.

Multiplexer 30 functions to sequentially couple each of leads 18-1, 18-2, 18-3, and 18-4 one at a time to internal conductor 34 of pacemaker 10. For example, and as shown in FIG. 3, a four-phase clock comprising individual phase signals $\phi_1$, $\phi_2$, $\phi_3$, and $\phi_4$ may be applied to multiplexer 30, such that lead 18-1 is coupled to conductor 34 during assertion of $\phi_1$, lead 18-2 is coupled to conductor 34 during assertion of $\phi_2$, and so on. It is believed that the design and implementation of multiplexer 30 would be a matter of routine to a person of ordinary skill in the circuit art. If clock signals $\phi_1$, $\phi_2$, $\phi_3$, and $\phi_4$ shown in FIG. 4 were applied to multiplexer 30, for example, each one of leads 18-1, 18-2, 18-3, and 18-4 would be coupled to conductor 34 for 1.95-mSec at a time, 128 times per second.

A pacing output circuit 36 is also shown in FIG. 3. The inventors have contemplated several different pacing arrangements for pacemaker 10. One or more of leads 18-1, 18-2, 18-3, and 18-4 could be utilized as both a pacing and sensing lead. This can be implemented in two ways: either multiplexer 30 may be controlled by signals $\phi_1$, $\phi_2$, $\phi_3$ and $\phi_4$ to apply pacing pulses produced on line 40 by pacing output circuit 36 to a selected one or more of leads 18-1, 18-2, 18-3, and 18-4; or pacing output circuit could provide pacing pulses on line 40' to a lead select circuit 42 adapted to convey pacing pulses on line 40' to a selected one or more of leads 18-1, 18-2, 18-3 and 18-4, the selection being indicated, for example, by means of control signals from pacemaker control circuitry not shown in FIG. 3.

Cardiac electrical signals from leads 18-1, 18-2, 18-3, and 18-4 are conducted on line 34 to a bandpass filter circuit 44, which in the presently disclosed embodiment of the invention comprises a high-pass filter made up of a capacitor 46 and a resistor 48, and a low-pass filter made up of resistor 50 and capacitor 52. In the presently preferred embodiment of the invention, bandpass filter 44 has a high-pass pole at 0.072-Hz and a low-pass pole at 182-Hz.

After filtering, cardiac signals from leads 18-1, 18-2, 18-3 and 18-4 are applied to a telemetry circuit 54. A telemetry circuit that is suitable for the purposes of the present invention is described in U.S. Pat. No. 4,556,063 issued to Thompson et al. on Dec. 3, 1985 entitled "Telemetry System for a Medical Device", which patent is hereby incorporated by reference in its entirety. Another telemetry system suitable for the purposes of the present invention is disclosed in U.S. patent application Ser. No. 07/765,475 in the name of Wyborny et al., entitled "Telemetry Format for Implanted Medical Device", which patent is also incorporated herein by reference in its entirety. Telemetry circuit 54 is coupled to a radio-frequency (RF) transmitting/receiving antenna 56 capable of transmitting signals to a compatible antenna 58 associated with external programmer 32. Programmer 32 may also have associated therewith various display devices such as a CRT 60 or a paper strip recorder 62, allowing a physician to view the telemetered EGM signal.

Further in accordance with the presently disclosed embodiment of the invention, pacemaker 10 is provided with a calibration circuit 64 coupled to conductor 34. As will be hereinafter described in greater detail, calibration circuit 64 is adapted to generate on conductor 34 known "test" or "reference" signals that may be applied to the pacemaker's telemetry channel. Upon receipt of this reference signal, external programmer 32 is thus able to automatically calibrate and auto-range the complete system, compensating for the effects of filter 44, pacemaker circuitry gain variability, telemetry system conversion inaccuracies, RF link decoding variations (i.e., "noise"), and peripheral ranging, signal reconstruction variations and inaccuracies.

According to one embodiment of the present invention, the reference signal generated by calibration circuit 64 is a 0.5-Hz square wave passed through a low pass filter at 10-mV amplitude, that is switched into the telemetry channel (i.e., onto conductor 34) for processing and transmission to programmer 32. Programmer 32 then uses the reference signal to calibrate the telemetry channel and automatically set the range of the received signal for display on CRT 60 or strip recorder 62. Calibration circuit 64 is also capable of producing a "differential wave" output reference signal, produced by differentiation of the square wave reference signal at each pulse edge. The "differential wave" signal thus comprises a stream of alternating positive and negative voltage spikes having a peak magnitude of ±10-mV. The maximum value of the differential signal, after transmission across the telemetry link, would be detected in programmer 32 using a peak detector for each polarity. The advantage of the "differential wave" reference signal is that it allows accurate, simultaneous dual-polarity calibration of the telemetry channel.

Figure 5:
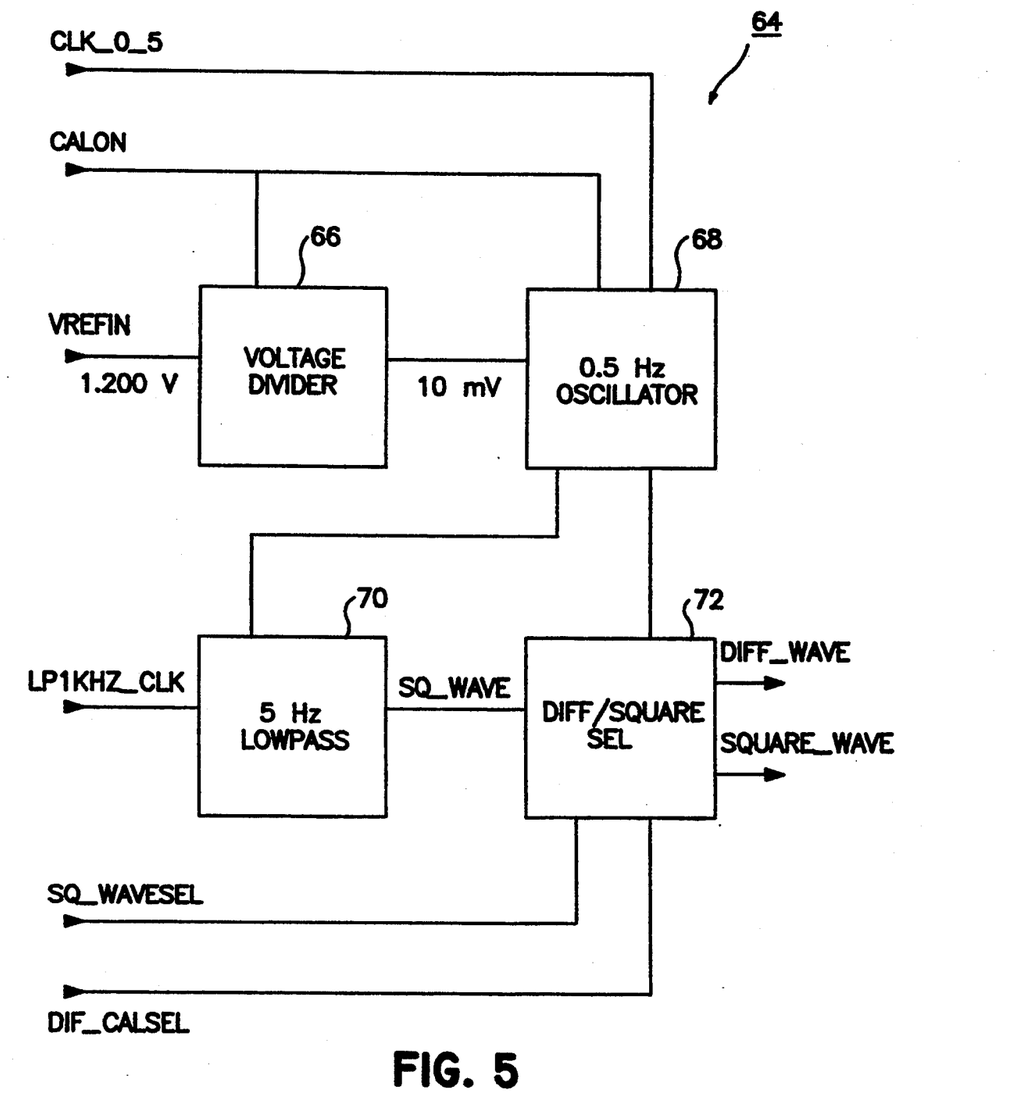
FIG. 5 is a block diagram of the calibration circuit of FIG. 3.

Referring now to FIG. 5, a block diagram of calibration circuit 64 is shown. It is to be understood in FIG. 5 that the various input signals to calibration circuit 64 are provided from elsewhere in the circuitry of pacemaker 10. For example, the signals SQ_WAVESEL and DIF_CALSEL are provided from controller circuitry (not shown) to enable selection of either a square-wave reference signal or a "differential wave" reference signal.

The VREFIN input signal to calibration circuit 64 is a 1.2-V reference voltage that is applied to voltage divider 66. Voltage divider 66 derives a regulated 10-mV signal that is applied to a 0.5-Hz oscillator circuit 68. It is believed by the inventors that the design and implementation of voltage divider circuit 66 would be a matter of routine to a person of ordinary skill in the circuit art. The CLK_0_5 input signal to oscillator 68 is a 0.5-Hz clock signal. The CALON input signal enables voltage divider 66 and oscillator 68; thus, when CALON is not asserted, voltage divider 66 and oscillator 68 are disabled and draw no bias current. This is particularly desirable in implanted medical devices, where power conservation is critical to maximum device longevity. Finally, the LP1KHZ_CLK input signal to calibration circuit 64 is a 1-kHz clock signal utilized by a 5-Hz low-pass filter circuit 70.

Figure 6:
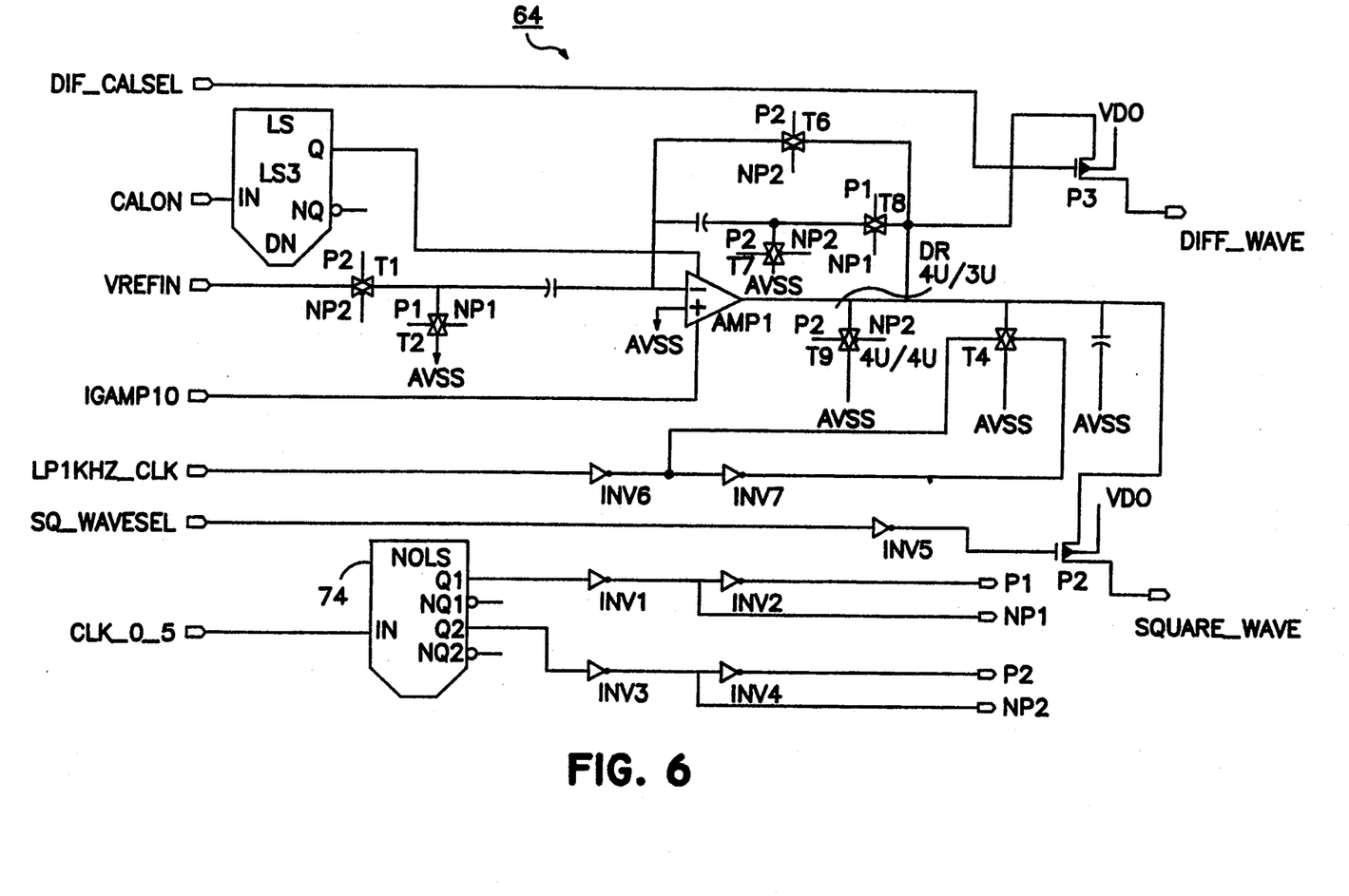
FIG. 6 is a schematic diagram of the calibration circuit of FIG. 3.

A schematic diagram of calibration circuit 64 is shown in FIG. 6. As shown in FIG. 6, a number of internal phase signals P1, NP1, P2, and NP2 are derived from the CLK_0_5 input signal as applied to a non-overlap (NOLS) shifter 74; these phase signals are used elsewhere in the calibration circuit, as shown in FIG. 6, to enable various transmission gates T1, T2, and so on.

With continued reference to FIG. 6, the CALON signal enables amplifier AMP1 prior to a calibration pulse. As would be appreciated by one of ordinary skill in the circuit art, AMP1 is an operational transconductance amplifier. The VREFIN voltage is sampled on capacitor C1 (which in the presently preferred embodiment of the invention has a capacitance of 1.14-pF) during phase 2 (i.e., when P2 is asserted). Also during P2, the offset for amplifier AMP1 is sampled on capacitor C5 (with capacitance of 120-pF) to implement a standard offset compensation scheme. During phase 1 (i.e., when P1 is asserted), the sampled voltage is divided by the ratio C1/C2. The DIF_CALSEL input enables transistor P3, allowing the calibration pulses output from AMP1 to appear on the DIFF_WAVE output line.

The SQ_WAVESEL input, when asserted, enables transistor P2, gating the calibration pulse output from AMP1 through a low-pass switched capacitor filter with a 5-Hz pole formed by $\frac{1}{2}\pi RC$ where $R = 1/fC$.

Figure 7:
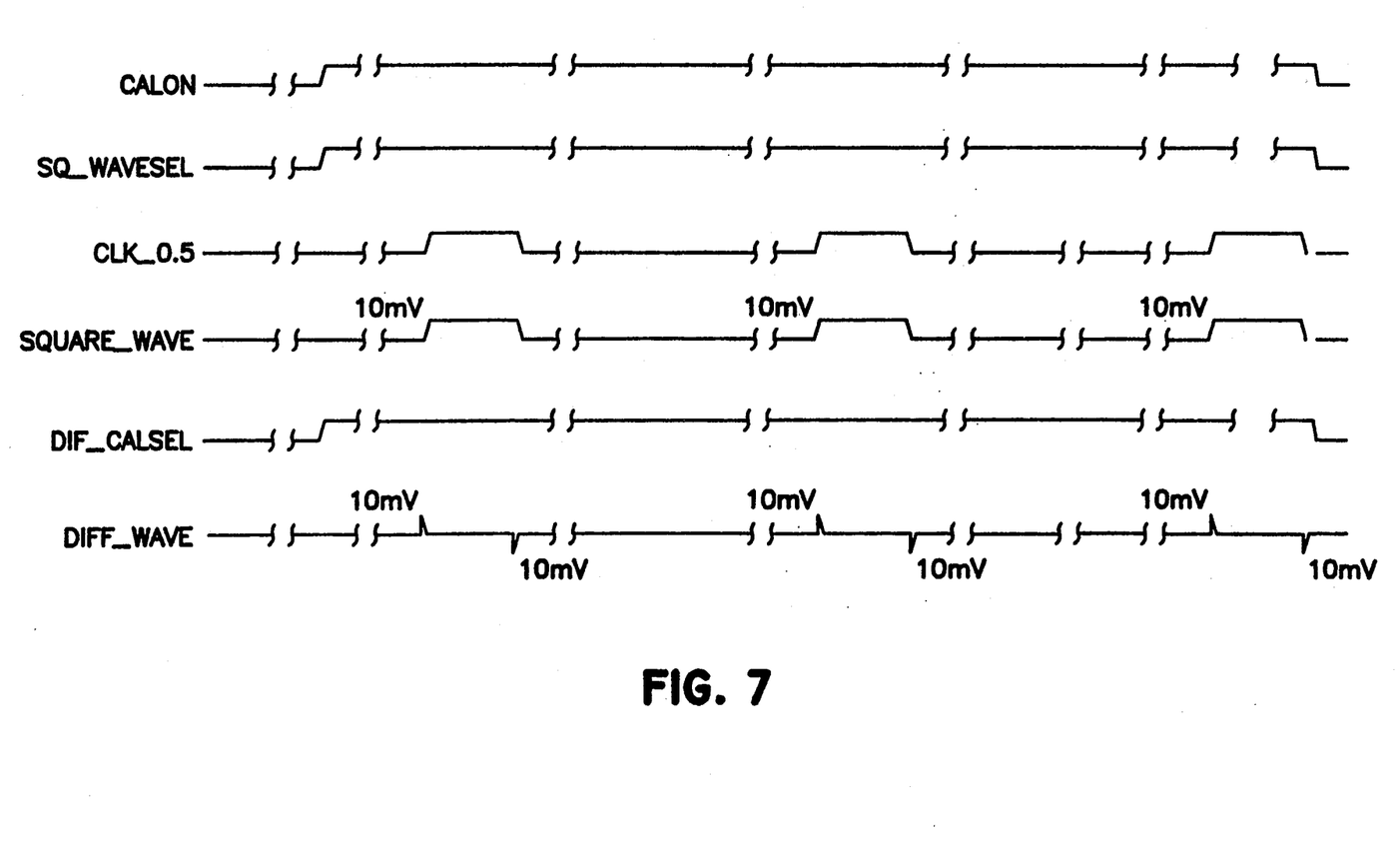
FIG. 7 is a timing diagram illustrating signals in the calibration circuit of FIG. 6.

A timing diagram illustrating the relationship between the various signals in the schematic diagram of FIG. 6 is shown in FIG. 7. As shown in FIG. 7, the SQUARE_WAVE output signal is a simple 0.5-Hz, 10-mV square wave, while the DIFF_WAVE output signal is a stream of alternating positive and negative spikes having peak voltages of 10-mV.

Figure 8A:
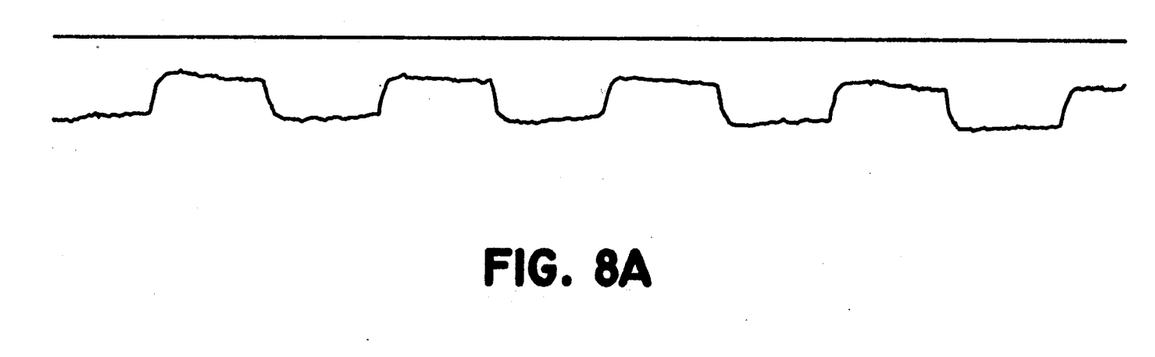
FIGS. 8a and 8b are timing diagrams illustrating the calibration signal after transmission to the programmer of FIG. 3.
Figure 8B:
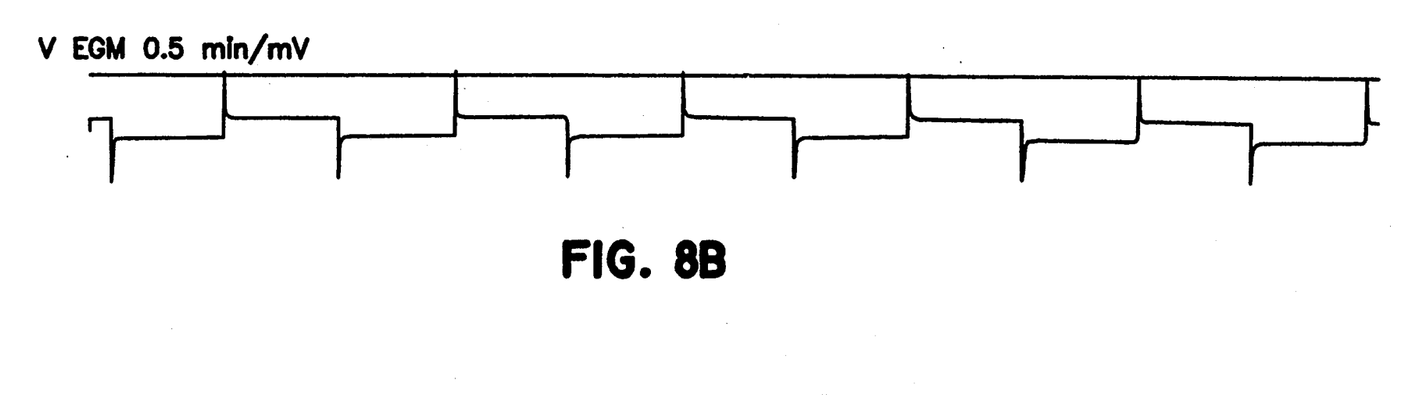

FIGS. 8a and 8b show what the SQUARE_WAVE and DIFF_WAVE output signals, respectively look like after having been transmitted by telemetry circuit 54 and printed on strip recorder 62. It is contemplated by the inventors that a comparison between the transmitted reference signal received by programmer 32 may be either automatically or manually analyzed for the purpose of determining the effect of the telemetry channel on transmitted signals. Thus, for example, the amount of attenuation of the transmitted signal can be detected (either manually, or by applying the transmitted signal to a threshold detector or the like) by comparing the transmitted signal with the known reference signal level.

As an alternative to transmitting the cardiac signals from leads 18-1, 18-2, 18-3, and 18-4 to an external peripheral as described above with reference to FIG. 3, it has been further contemplated by the inventors that heart transplant monitoring may be accomplished by providing in pacemaker 10 circuitry for storing long-term averages of peak values of those signals. These stored values could be subsequently transmitted to the external device for analysis. An implantable device capable of computing long-term average values of various diagnostic values is extensively described in pending U.S. patent application Ser. No. 07/881,996 filed on May 1, 1992 by Nichols et al., entitled "Diagnostic Function Data Storage and Telemetry Out for Rate Responsive Cardiac Pacemaker", which application is hereby incorporated by reference in its entirety.

The inventors have also contemplated a further refinement of the presently disclosed embodiment of the invention, wherein an internal clock in pacemaker 10 would enable amplitude evaluation as described hereinabove at periodic intervals, for example, every twenty-four hours. By performing the amplitude evaluation only at periodic intervals, advantages in memory and battery efficiency may be realized. In addition, this arrangement would provide a method of obtaining a stable baseline of the values, since the effects of normal short-term or cycle-to-cycle variations in the cardiac signal would be minimized. As an example, the amplitude evaluation could occur during the middle of the night to ensure the patient is at rest.

Still another refinement to the presently disclosed embodiment of the invention has been contemplated, wherein an activity sensor is also provided in pacemaker 10. As noted in the above-referenced Rosenbloom article, exercise-induced regional ischemia may also produce abrupt and substantial declines in the peak R-wave, which may be erroneously interpreted as indicating rejection. If the present invention were practiced with a pacemaker having an activity sensor, however, exercise-induced R-wave variations could be readily distinguished from the decline in peak R-wave amplitudes associated with rejection by sampling data during periods of patient inactivity.

Still another refinement to the presently disclosed embodiment of the invention has been contemplated, wherein electrodes 18-1, 18-2, 18-3, and 18-4 of FIG. 2 are sequentially paced unipolarly with respect to the can of pacemaker 10. The three non-paced electrodes monitor the wavefront propagation as the ventricles depolarize. Each sensing lead monitors a different summation of conducted wavelets and, by monitoring the signal arrival at each sensing site, cardiac conduction velocity and intrinsic cardiac tissue status may be monitored. This concept of sensing twelve different sensing configurations allows for a more complete monitoring of cardiac tissue than the hereinabove-described four-site intrinsic waveform monitoring.

From the foregoing detailed description of a specific embodiment of the invention, it should be apparent that a method and apparatus for calibrating a telemetry channel has been disclosed. The disclosed method and apparatus are particularly well-suited to the situation in which an implanted cardiac device is used to transmit electrical cardiac signals to an external device, for the purpose of monitoring changes in peak amplitude of the cardiac signals. Such changes, as previously noted can be indicative of certain cardiac conditions, such as rejection of a transplanted heart.

Although a particular embodiment of the present invention has been disclosed herein in some detail, it is to be understood that this has been done for the purposes of illustration only, and is not intended to limit the scope of the present invention as defined in the appended claims. It is believed by the inventors that various alterations, modifications, and substitutions may be made to the disclosed embodiment of the invention without departing from the spirit and scope of the invention. In particular, while in the disclosed embodiment a reference signal having a known amplitude is transmitted on the telemetry channel in order to determine whether any attenuation of the reference signal amplitude has occurred in the telemetry channel, it is also contemplated by the inventors that other types of reference signals, for instance sinusoidal signals or the like, may be provided in order to additionally assess the telemetry channel's effect on the phase or frequency spectrum of the reference signal.

What is claimed is:

1. An implantable medical device having a telemetry system for communicating analog signals to an external peripheral device, said telemetry system being coupled to a source of electrical cardiac signals, and said telemetry system comprising:
   a calibration circuit means for generating a reference signal having at least one known attribute;
   a filter circuit, comprising means for alternately coupling to said calibration circuit and said cardiac signal source, and means for filtering said reference signal and said cardiac signal;
   an encoding circuit means coupled to said filter circuit, for digitally encoding said filtered signals; and
   a transmitter means coupled to said encoding circuit, for transmitting said digitally encoded signals to said external peripheral device to allow for determination of a difference with respect to said attribute between said transmitted reference signal and said reference signal;
   wherein said reference signal is a square wave comprising a stream of square pulses and wherein said at least one known attribute of said reference signal is the amplitude of said pulses.

2. An implantable medical device having a telemetry system for communicating analog signals to an external peripheral device, said telemetry system being coupled to a source of electrical cardiac signals, and said telemetry system comprising:
   a calibration circuit means for generating a reference signal having at least one known attribute;
   a filter circuit comprising means for alternately coupling to said calibration circuit and said cardiac signal source, and means for filtering said reference signal and said cardiac signal;
   an encoding circuit means coupled to said filter circuit, for digitally encoding said filtered signals; and
   a transmitter means coupled to said encoding circuit, for transmitting said digitally encoded signals to said external peripheral device to allow for determination of a difference with respect to said attribute between said transmitted reference signal and said reference signal;
   wherein said reference signal is a square wave comprising a stream of square pulses, and wherein said at least one known attribute is pulse width.

3. An implantable medical device having a telemetry system for communicating analog signals to an external peripheral device, said telemetry system being coupled to a source of electrical cardiac signals, and said telemetry system comprising:
   a calibration circuit means for generating a reference signal having at least one known attribute;
   a filter circuit comprising means for alternately coupling to said calibration circuit and said cardiac signal source, and means for filtering said reference signal and said cardiac signal;
   an encoding circuit means coupled to said filter circuit, for digitally encoding said filtered signals; and
   a transmitter means coupled to said encoding circuit, for transmitting said digitally encoded signals to said external peripheral device to allow for determination of a difference with respect to said attribute between said transmitted reference signal and said reference signal;
   wherein said reference signal comprises stream of alternating positive and negative spikes, and wherein said at least one known attribute is peak spike magnitude.

4. An implantable medical device having a telemetry system for communicating analog signals to an external peripheral device, said telemetry system being coupled to a source of electrical cardiac signals, and said telemetry system comprising:
   a calibration circuit means for generating a reference signal having at least one known attribute;
   a filter circuit comprising means for alternately coupling to said calibration circuit and said cardiac signal source, and means for filtering said reference signal and said cardiac signal;
   an encoding circuit means coupled to said filter circuit for digitally encoding said filtered signals; and
   a transmitter means coupled to said encoding circuit, for transmitting said digitally encoded signals to said external peripheral device to allow for determination of a difference with respect to said attribute between said transmitted reference signal and said reference signal.
   wherein said reference signal comprises a sinusoidal waveform and wherein said at least one known attribute is amplitude.

5. A method for quantifying an unpredictable attenuation factor in a telemetry channel between an implanted medical device and an external receiver, comprising the steps of:
   (a) generating, in said implantable device, a reference signal having a known amplitude;
   (b) transmitting said reference signal through said telemetry channel;
   (c) comparing, in said receiver, an amplitude of said reference signal transmitted through said telemetry channel in step (b) with said known amplitude.

6. A method in accordance with claim 5, wherein said reference signal is a square wave.

7. A method in accordance with claim 5, wherein said reference signal is a stream of alternating positive and negative spikes.

8. A method in accordance with claim 5, wherein said reference signal is a sinusoidal wave.

9. A heart transplant monitoring system, comprising:
   a plurality of implanted epicardial leads, electrically coupled to a patient's heart, comprising means for conducting electrical cardiac signals;
   an implanted telemetry system means coupled to said plurality of leads, for transmitting said electrical cardiac signals to an external receiver;

signal processing means coupled to said external receiver for detecting a reduction in said electrical cardiac signals indicative of heart rejection; and an implanted activity sensing circuit means for producing an activity signal corresponding to detected levels of patient activity;

wherein said implanted telemetry system means comprises means for transmitting said electrical cardiac signals to said external receiver only when said activity signal indicates that said patient is at rest.

* * * * *